United States Patent [19]

Reale, Jr. et al.

[11] Patent Number: 4,961,855

[45] Date of Patent: * Oct. 9, 1990

[54] DEHYDRATION OF ORGANIC OXYGENATES

[75] Inventors: John Reale, Jr.; Craig R. Bartels, both of Wappingers Falls, N.Y.

[73] Assignee: Texaco Inc., White Plains, N.Y.

[ * ] Notice: The portion of the term of this patent subsequent to Jan. 17, 2006 has been disclaimed.

[21] Appl. No.: 279,398

[22] Filed: Dec. 5, 1988

Related U.S. Application Data

[63] Continuation-in-part of Ser. No. 97,766, Sep. 17, 1987, Pat. No. 4,802,988.

[51] Int. Cl.$^5$ .............................................. B01D 13/00
[52] U.S. Cl. ...................................... 210/640; 55/16; 55/158
[58] Field of Search ................... 55/16, 158; 210/634, 210/640, 644, 649–652, 653, 654

[56] References Cited

U.S. PATENT DOCUMENTS 4,755,299  7/1988  Brüschke ............................. 55/16
4,798,674  1/1989  Pasternak et al. .................. 55/158

Primary Examiner—Frank Sever
Attorney, Agent, or Firm—Robert A. Kulason; James J. O'Loughlin; Carl G. Seutter

[57] ABSTRACT

Concentration of aqueous solutions of isopropanol may be effected by a composite membrane including a glutaraldehyde cross-linked polyvinyl alcohol bonded to a porous layer of polysulfone on a polyester backing.

18 Claims, No Drawings

DEHYDRATION OF ORGANIC OXYGENATES

This patent application is a continuation-in-part of application Ser. No. 97,766 filed Sept. 17, 1987, now U.S. Pat. No. 4,802,988.

FIELD OF THE INVENTION

This invention relates to the dehydration of organic oxygenates such as isopropyl alcohol. More particularly it relates to a membrane technique for effecting separation of water from an aqueous mixture containing isopropyl alcohol.

BACKGROUND OF THE INVENTION

As well known to those skilled in the art, it is possible to remove water from mixtures thereof with organic liquids by various techniques including adsorption or distillation. These conventional processes, particularly distillation, are however, characterized by high capital cost. In the case of distillation for example the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling—plus pumping, etc.

Furthermore the properties of the materials being separated, as is evidenced by the distillation curves, may be such that a large number of plates may be required, etc. when the material forms an azeotrope with water, additional problems may be present which for example, would require that separation be effected in a series of steps (e.g. as in two towers) or by addition of extraneous materials to the system.

There are also comparable problems which are unique to adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane. The permeate is then removed as a vapor from the downstream side of the film—typically by sweeping with a carrier gas or by reducing the pressure below the saturated vapor pressure of the permeating species.

Illustrative membranes which have been employed in prior art techniques include those set forth in the following table:

TABLE

| Separating Layer | References |
| --- | --- |
| Nafion brand of perfluorosulfonic acid | Cabasso and Liu J. Memb. Sci. 24, 101 (1985) |
| Sulfonated polyethylene | Cabasso, Korngold & Liu J. Pol. Sc: Letters, 23, 57 (1985) |
| Fluorinated polyether or Carboxylic Acid fluorides | USP 4,526,948 to Dupont as assignee of Resnickto |
| Selemion AMV brand of Asahi Glass cross-linked styrene butadiene (with quaternary ammonium residues on a polyvinyl chloride backing) | Wentzlaff Boddeker & Hattanbach J. Memb. Sci. 22,333 (1985) |
| Cellulose triacetate | Wentzlaff, Boddeker & Hattanback, J. Memb. Sci. 22, 333 (1985) |
| Polyacrylonitrile | Neel, Aptel & Clement Desalination 53, 297 (1985) |
| Crosslinked Polyvinyl Alcohol | Eur. Patent 0 096 339 to GFT as assignee of Bruschke |
| Poly(maleimide-acrylonitrile) | Yoshikawa et al J. Pol. Sci. 22, 2159 (1984) |
| Dextrine isophorodisocyanate | Chem. Econ. Eng. Rev., 17, 34 (1985) |

The cost effectiveness of a membrane is determined by the selectivity and productivity. Of the membranes commercially available, an illustrative membrane of high performance is that disclosed in European patent No. 0 096 339 A2 of GFT as assignee of Bruschke—published 21 Dec. 1983.

European Patent No. 0 096 339 A2 to GFT as assignee of Bruschke discloses, as cross-linking agents, diacids (typified by maleic acid or fumaric acid); dihalogen compounds (typified by dichloroacetone or 1,3-dichloroisopropanol); aldehydes, including dialdehydes, typified by formaldehyde. These membranes are said to be particularly effective for dehydration of aqueous solutions of ethanol or isopropanol.

This reference discloses separation of water from alcohols, ethers, ketones, aldehydes, or acids by use of composite membranes. Specifically the composite includes (i) a backing typically about 120 microns in thickness, on which is positioned (ii) a microporous support layer of a polysulfone or a polyacrylonitrile of about 50 microns thickness, on which is positioned (iii) a separating layer of cross-linked polyvinyl alcohol about 2 microns in thickness.

Polyvinyl alcohol may be cross-linked by use of difunctional agents which react with the hydroxyl group of the polyvinyl alcohol. Typical cross-linking agent may include dialdehydes (which yield acetal linkages), diacids or diacid halides (which yield ester linkages), dihalogen compounds or epichlorhydrin (which yield ether linkages) olefinic aldehydes (which yield ether/acetal linkages), boric acid (which yields boric ester linkages), sulfonamidoaldehydes, etc.

See also J. G. Prichard, *Polyvinyl Alcohol, Basic Properties and Uses*, Gordon and Breach Science Publishers, New York (1970) or C. A. Finch, *Polyvinyl Alcohol, Properties and Applications*, John Wiley and Sons, New York (1973).

U.S. Pat. No. 4,728,429 to Cabasso et al, U.S. Pat. No. 4,067,805 to Chiang et al, U.S. Pat. No. 4,526,948 to Resnick, U.S. Pat. No. 3,750,735 to Chiang et al, and U.S. Pat. No. 4,690,766 to Linder et al provide additional background.

It is an object of this invention to provide a novel composite membrane characterized by its ability to effect separation of water from organic oxygenates such as isopropyl alcohol. Other objects will be apparent to those skilled in the art.

STATEMENT OF THE INVENTION

In accordance with certain of its aspects, this invention is directed to a method of concentrating an aqueous charge including an organic oxygenate which comprises maintaining a non-porous separating layer of cast polyvinyl alcohol which has been cross-linked with an aliphatic polyaldehyde containing at least three carbon atoms including those in said aldehyde groups;

maintaining a pressure drop across said non-porous separating layer of polyvinyl alcohol;

passing an aqueous charge including an organic oxygenate into contact with the high pressure side of said non-porous separating layer of polyvinyl alcohol whereby at least a portion of said water in said charge and a lesser portion of organic oxygenate in said charge pass by pervaporation through said non-porous separating layer of polyvinyl alcohol as a lean mixture containing more water and less organic oxygenate than are present in said charge and said charge is converted to a rich liquid containing less water and more organic oxygenate than are present in said charge;

recovering from the low pressure side of said non-porous separating layer of polyvinyl alcohol said lean mixture containing more water and less organic oxygenate than are present in said charge, said lean mixture being recovered in vapor phase at a pressure below the vapor pressure thereof; and recovering from the high pressure side of said non-porous separating layer said rich liquid containing a lower water content and a higher organic oxygenate content than are present in said charge.

In accordance with certain of its other aspects, this invention is directed to a non-porous separating layer of thickness of 1-10 microns of cast polyvinyl alcohol of molecular weight $\overline{M}_n$ of 20,000-200,000 which has been cross-linked, in the presence of acid catalyst, with an aliphatic polyaldehyde containing at least three carbon atoms including those in said aldehyde groups and thereafter cured at 100° C.-225° C.

DESCRIPTION OF THE INVENTION

The composite structure of this invention includes a multi-layer assembly which in the preferred embodiment preferably includes a porous carrier layer which provides mechanical strength and support to the assembly.

THE CARRIER LAYER

This carrier layer, when used, is characterized by its high degree of porosity and mechanical strength. It may be fibrous or non-fibrous, woven or non-woven. In the preferred embodiment, the carrier layer may be a porous, flexible, non-woven fibrous polyester.

A preferred non-woven polyester carrier layer may be formulated of non-woven, thermally-bonded strands and characterized by a fabric weight of 80±8 grams per square yard, a thickness of 4.2±0.5 mils, a tensile strength (in the machine direction) of 31 psi and (in cross direction) of 10 psi, and a Frazier air permeability of 6 cuft/min/sq. ft. @0.5 inches of water.

THE POROUS SUPPORT LAYER

The porous support layer of this invention is preferably formed of a sheet of polysulfone polymer or less preferably of polyacrylonitrile. Typically the polysulfone may be of thickness of 40-80 microns, say 50 microns and of molecular weight $\overline{M}_n$ of 5,000-100,000, preferably 20,000-60,000 say 40,000. The polysulfone is preferably characterized by a pore size of less than about 500A and typically about 200A. This corresponds to a molecular weight cut-off of less than about 25,000 typically about 20,000.

The sulfone polymers which may be employed may include those made from cumene containing isopropylidene groups in the backbone; e.g.

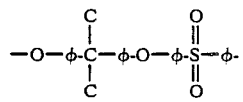

These isopropylidene sulfones containing repeating units including ether-aromatic-isopropylidene-aromatic-ether-aromatic-sulfone-aromatic groups may typically have a molecular weight $\overline{M}_n$ of 15,000-30,000, a water absorption (at 20° C.) of about 0.85 w %, a glass transition temperature of 449° K., a density of 1.25 mg/m³, a tensile strength (at 20° C.) at yield of 10,000 psi, and a coefficient of linear thermal expansion of $2.6 \times 10^{-5}$ mm/mm/° C.

It is found, however, that the preferred sulfone polymers which may be employed in practice of the process of this invention, may include those which are free of isopropylidene moieties in the backbone chain and wherein the phenylene group in the backbone are bonded only to ether oxygen atoms and to sulfur atoms. These preferred polymers, which may be typically, be prepared from

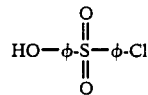

may be characterized by a backbone containing the following repeating group:

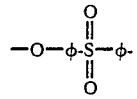

A preferred sulfone polymer may be a polyether sulfone which is free of isopropylidene moieties in the backbone chain and wherein the phenylene groups in the backbone are bonded only to ether-oxygen atoms and to sulfur atoms. This polymer may be characterized by molecular weight $M_n$ of 25,000, water absorption @20° C. of 2.1 w %, glass transition temperature of 487° K., tensile strength at yield of 12,200 psig at 20° C.; and coefficient of linear thermal expansion of $5.5 \times 10^{-5}$ mm/mm/° C. This polymer has a molecular weight cut off of about 20,000 and has a pore size of about 200A.

THE SEPARATING LAYER

The separating layer which permits attainment of the separation in accordance with this invention includes a non-porous film of cross-linked polyvinyl alcohol of thickness of about 1-10 microns preferably 1-5 microns, say 3 microns. The layer is formed from polyvinyl alcohol which has been prepared by hydrolysis of polyvinyl acetate-typically 50-100% hydrolyzed, preferably 90-100%, say 100% hydrolyzed. The charge polyvinyl alcohol has a molecular weight of 20,000-200,000 say 115,000. Typically it may be employed as a 5-10 w %, say 7 w % aqueous solution. A commercially available product which may be employed is the Aldrich brand of 100% hydrolyzed polyvinyl alcohol of molecular weight of about 115,000 as a 7 w % aqueous solution.

It is a feature of this invention that the membrane or sheet of cross-linked polyvinyl alcohol separating layer is formed in situ on the porous support layer. This is effected by use, as a cross-linking agent, of an aliphatic dialdehyde containing at least three carbon atoms. Preferably the aliphatic dialdehyde may contain 3-8, commonly 3-6, carbon atoms, most preferably 5 carbon atoms. Typical alphatic dialdehydes which may be employed may include:

TABLE glutaraldehyde
2-hydroxyhexanedial-1,6
malonic dialdehyde
succinic dialdehyde
hexanedial-1,6

The preferred aliphatic dialdehyde is glutaraldehyde. Aldehydes falling outside the scope of this invention typified by formaldehyde, glyoxal, or succinic semialdehyde yield membranes which are characterized by unsatisfactory performance. Performance is judged by the ability of a membrane system to give a permeate containing decreased content of organic oxygenate (from a charge containing a higher content of organic oxygenate and water) with a good flux (kilograms-/meter$^2$-/hour (kmh)) at a predetermined feed temperature and with a vacuum on the permeate side and a condenser cooled by liquid nitrogen). Compositions falling outside the scope of this invention may be characterized by unsatisfactory separation or unsatisfactory productivity (flux) or both.

In situ cross-linking may be carried out by casting 5-10 w %, say 7 w % aqueous solution of polyvinyl alcohol which contains the aliphatic dialdehyde cross-linking agent. The mole ratio of cross-linking agent to polyvinyl alcohol may be 0.05-0.30, say 0.2.

Cross-linking is carried out, in the presence of acid catalyst, preferably inorganic acid. Sulfuric acid is preferred. Hydrochloric acid is much less preferred—because it yields membranes of poor separation, although the flux may be high.

It may be possible in one embodiment to cross-link the polyvinyl alcohol separating layer in one step by adding to the aqueous solution of polyvinyl alcohol and dialdehyde, the acid catalyst, preferably sulfuric acid, in mole ratio of acid to dialdehyde of 0.08-0.14, say 0.1.

In another embodiment, it may be possible to apply to the porous support layer, an aqueous invention of polyvinyl alcohol and dialdehyde. This may be dried at 40° C.-80° C., say 50° C. for 2-10 minutes, say 4 minutes to form a film. There may then be added onto the surface of this film a viscous solution containing 2-7 w %, say 3.5 w % of polyvinyl alcohol and having a mole ratio of sulfuric acid to dialdehyde of 0.08-0.14, preferably 0.1.

The composite membrane, whether prepared by the one-step or the two-step process may then be cured in an oven at 100° C.-200° C., say 125° C. for 1-30 minutes, say 2 minutes to yield a polyvinyl alcohol film having a thickness of 1-10 microns, say 3 microns.

THE COMPOSITE MEMBRANE

It is a feature of this invention that the composite membrane of this invention may comprise (i) an optional carrier layer, characterized by porosity and mechanical strength, for supporting a porous support layer and a separating layer, (ii) a polysulfone porous support layer of molecular weight of 5,000-100,000, of thickness of 10-80 microns, and of molecular weight $\overline{M}_n$ cut off of 25,000-100,000 and (iii) as a non-porous separating layer polyvinyl alcohol of molecular weight of 20,000-200,000 which has been cross-linked with an aliphatic dialdehyde containing 3-9 carbon atoms.

The composite membranes of this invention may be utilized in various configurations. It is, for example, possible to utilize the composite in a plate-and-frame configuration in which separating layers may be mounted on the porous support layer with the carrier layer.

It is possible to utilize a spiral mound module which includes a non-porous separating layer membrane mounted on a porous support layer and a carrier layer, the assembly being typically folded and bonded or sealed along all the edges but an open edge—to form a bag-like unit which preferably has the separating layer on the outside. A cloth spacer, serving as the permeate or discharge channel is placed within the bag-like unit. The discharge channel projects from the open end of the unit.

There then placed on one face of the bag-like unit, adjacent to the separating layer, and coterminous therewith, a feed channel sheet—typically formed of a plastic net.

The so-formed assembly is wrapped around a preferably cylindrical conduit which bears a plurality of perforations in the wall—preferably in a linear array which is as long as the width of the bag-like unit. The projecting portion of the discharge channel of the bag-like unit is placed over the performations of the conduit; and the bag-like unit is wrapped around the conduit to form a spiral wound configuration.

It will be apparent that, although only one feed channel is present, the single feed channel in the wound assembly will be adjacent to two faces of the membrane layer. The spiral wound configuration may be formed by wrapping the assembly around the conduit a plurality of times to form a readily handleable unit. The unit is fitted within a shell (in manner comparable to a shell-and-tube heat exchanger) provided with an inlet at one end and an outlet at the other. A bafflelike seal between the inner surface of the shell and the outer surface of the spiral-wound input prevents fluid from bypassing the operative membrane system and insures that fluid enters the system principally at one end. The permeate passes from the feed channel, into contact with the separating layer and thence therethrough, into the permeate channel and thence therealong to and through the perforations in the conduit through which it is withdrawn as net permeate.

In use of the spiral wound membrane, charge liquid is permitted to pass through the plastic net which serves as a feed channel and thence into contact with the non-porous separating membranes. The liquid which does not pass through the membranes is withdrawn as retentate. The liquid or vapor which permeates the membrane passes into the volume occupied by the permeate spacer and through this permeate channel to the perforations in the cylindrical conduit through which it is withdrawn from the system. In this embodiment, it will be apparent that the system may not include a carrier layer.

In another embodiment, it is possible to utilize the system of this invention as a tubular or hollow fibre. In this embodiment, the polysulfone porous support layer may be extruded as a fine tube with a wall thickness of typically 0.001-0.1 mm. The extruded tubes are passed through a bath of polyvinyl alcohol which is cross-linked and cured in situ. A bundle of these tubes is secured (with an epoxy adhesive) at each end in a header; and the fibres are cut so that they are flush with the ends of the header. This tube bundle is mounted within a shell in a typical shell-and-tube assembly.

In operation, the charge liquid is admitted to the tube side and passes through the inside of the tubes and exits as retentate. During passage through the tubes, permeate passes through the non-porous separating layer and permeate is collected in the shell side.

In this embodiment, it will be apparent that the system may not normally include a carrier layer. In still another embodiment, the porous support layer may be omitted; and the separating layer is extruded and thereafter cross-linked and cured in situ prior to mounting in the headers.

PERVAPORATION

It is a feature of the non-porous polyvinyl alcohol separating layer that it is found to be particularly effective when used in a pervaporation process. In pervaporation, a charge liquid containing a more permeable and a less permeable component is maintained in contact with a non-porous separating layer; and a pressure drop is maintained across that layer. The charge liquid dissolves into the membrane and diffuses therethrough. The permeate which passes through the membrane and exits as a vapor may be recovered by condensing at low temperature or alternatively may be swept away by use of a moving stream of gas. Preferably, the permeate side of the membrane is maintained at a low pressure, typically 5 mm. Hg.

For general background on pervaporation, note U.S. Pat. Nos. 4,277,344; 4,039,440; 3,926,798; 3,950,247; 4,035,291; etc.

It is a feature of the process of this invention that the novel membrane may be particularly useful in pervaporation processes for dewatering aqueous mixtures of organic oxygenates. It may be possible to utilize the process of this invention to remove water from immiscible mixtures therewith as in the case of ethyl acetate (solubility in water at 15° C. of 8.5 parts per 100 parts of water). It will be apparent to those skilled in the art that it may be desirable to separate large quantities of water from partially miscible systems as by decantation prior to utilizing the process of the invention to remove the last traces of water.

The advantages of the instant invention are more apparent when the charge liquid is a single phase homogeneous aqueous solution as is the case for example with isopropanol. The system may also find use in the case of slightly soluble liquids wherein two phases are present (i) water-oxygenate first phase and, as a second phase (ii) either water or oxygenate. Clearly those charge liquids which contain only a small portion of an immiscible second liquid phase may benefit most from the process of this invention. It is also a feature of this invention that it may be particularly useful to separate azeotropes such as isopropanol-water.

The charge organic oxygenates which may be treated by the process of this invention may include alcohols, glycols, acids, esters, ketones, aldehydes, etc. It will be apparent to those skilled in the art that the charge organic oxygenates used should be inert with respect to the separating membrane. Clearly a system wherein the membrane is attacked by the components of the charge liquid will not yield significant separation for any reasonable period of time. Best results may be achieved when treating alcohols (such as isopropanol) or glycols (such as ethylene glycol). Results achieved with acids are generally less satisfactory.

Illustrative alcohols may include ethanol, propanol, n-butanol, i-butanol, t-butanol, amyl alcohols, hexyl alcohols, etc.

Illustrative glycols may include ethylene glycol, propylene glycols, butylene glycol or glycol ethers such as diethylene glycol, triethylene glycol, or triols, including glycerine; etc.

Illustrative acids may include formic acid, oxalic acid, acetic acid, propionic acid, etc.

Illustrative esters may include ethyl acetate, methyl acetate, butyl acetate, methyl benzoate, ethylene glycol mono acetate, propylene glycol monostearate, etc.

Illustrative ethers may include tetrahydroforan, diethyl ether, and diisopropyl ether.

Illustrative ketones may include acetone, methyl ethyl ketone, acetophenone, etc.

Illustrative aldehydes may include formaldehyde, acetaldehyde, propionaldehyde, etc.

It is believed that the advantages of this invention are most apparent where the organic oxygenate is a liquid which is infinitely miscible with water—typified by isopropyl alcohol.

A typical charge may be an aqueous solution containing 70%–95%, say 80 w % isopropanol.

In practice of the pervaporation process of this invention, the charge aqueous organic oxygenate solution typically at 40° C.–120° C., say 80° C. may be passed into contact with the non-porous separating layer of the membrane of this invention. A pressure drop of about one atmosphere is commonly maintained across the membrane. Typically, the feed or charge side of the membrane is at about atmospheric pressure and the permeate or discharge side of the membrane is at a pressure of about 2–50 preferably 5–20, say 10 mm. Hg.

The permeate which passes through the membrane includes water and a small proportion of the organic oxygenate from the charge liquid. Typically, the permeate contains 90–99.0, say 99 w % water. Permeate is recovered in vapor phase.

Pervaporation may typically be carried out at a flux of 0.01–10, say 0.50 gallons per square foot per day which corresponds to about 0.17–16.9, say 0.68 kilograms per square meter per hour (kmh). Typically, the units may show good separation (measured in terms of w % organic oxygenate in the permeate during pervaporation of an aqueous solution of organic oxygenate through a polyvinyl alcohol separating layer.

Practice of the process of this invention will be apparent to those skilled in the art from inspection of the following examples wherein, as elsewhere in this specification, all parts are parts by weight unless otherwise stated. An asterisk indicates a control example.

DESCRIPTION OF SPECIFIC EMBODIMENTS

EXAMPLE I

In this example, which represents the best mode presently known of carrying out the process of this invention, the selective separating layer is mounted on the porous support layer of a commercially available (from Film Tec Corp) composite containing a non-woven polyester backing as carrier layer, bearing as porous support layer, a microporous polysulfone layer of molecular weight cut-off of 20,000.

The separating layer is formed in a two step process. In the first step a 7 w % aqueous solution of polyvinyl alcohol (m.w. 115,000) containing glutaraldehyde (mole ratio of glutaraldehyde to polyvinyl alcohol of 0.21) is applied to the polysulfone layer to form a 1.5 mil film. The composite is heated to 50° C. for 4 minutes.

A second coat is then applied by a 5 w % aqueous solution of polyvinyl alcohol (m.w. 115,000) containing sulfuric acid (mole ratio of sulfuric acid to polyvinyl alcohol of 0.027) to form a film of 1.5 mil thickness. The composite is heat treated at 125° C. for 2 minutes.

The membrane made by this two-step method is evaluated in a pervaporation cell to which the charge is admitted at 70° C. Permeate pressure is 8 torr at liquid nitrogen temperature.

In this preferred embodiment, the charge solution is an 85 w % aqueous solution of isopropanol. The permeate condenser contains an aqueous solution containing only 0.95 w % isopropanol. The Flux (kmh) is 1.004.

EXAMPLE II

In this Example, the procedure of Example I is carried out, except that the charge solution is a 93.3 w % solution of isopropanol at 70° C. The permeate condenser contains only 0.56 w % isopropanol. The Flux is 0.18.

The results attained in Example I-II may be tabulated as follows:

TABLE

| | | ISOPROPANOL | | |
| | | Feed | Permeate | |
| Example | Membrane of Exam | Conc % IPA | Conc % IPA | Flux Kmh |
| --- | --- | --- | --- | --- |
| I | I | 85 | 0.95 | 1.004 |
| II | I | 95.3 | 0.56 | 0.18 |

From this table it is apparent that in the preferred embodiment, it is possible to obtain an extremely high flux; and it is possible to effect concentration of an 85 w % aqueous solution of isopropanol by removal of water therefrom, the permeate containing less than 1 w % isopropanol.

EXAMPLES III-VI

In this series of examples, the procedure of Example I is followed except that the second coat is applied from a 3.5 w % aqueous solution of polyvinyl alcohol (m.w. 115,000) containing sulfuric acid (mole ratio of sulfuric acid to polyvinyl alcohol of 0.037) to form a film of 1.9 mil thickness. The composite is heat treated at 125° C. for 2 minutes.

This system is evaluated at 70° C. as in Example I to yield, in the permeate condenser, an aqueous solution of isopropanol. The feed concentration, the concentration of isopropanol in the permeate condenser, and the flux are tabulated infra.

The results attained in Examples III-VI may be tabulated as follows:

TABLE

| | | ISOPROPANOL | | |
| | | Feed | Permeate | |
| Example | Membrane of Exam | Conc % IPA | Conc % IPA | Flux Kmh |
| --- | --- | --- | --- | --- |
| III | III | 75.7 | 5.0 | 0.99 |
| IV | III | 85.0 | 1.4 | 0.57 |
| V | III | 95.3 | 0.45 | 0.52 |

TABLE-continued

| | | ISOPROPANOL | | |
| | | Feed | Permeate | |
| Example | Membrane of Exam | Conc % IPA | Conc % IPA | Flux Kmh |
| --- | --- | --- | --- | --- |
| VI | III | 98.6 | 0.60 | 0.009 |

From this table, it is apparent that it is possible to separate water permeate (containing only small concentrations of isopropanol) and to thus obtain retentate of increased concentration of isopropanol. It is noted that over most of the range, as the concentration of isopropanol in the charge increases from 75.7 w % to 95.3 w %, the concentration of isopropanol in the permeate desirably decreases and the Flux remains reasonably high.

EXAMPLES VII*-X*

In this series of control Examples, the separating layer is a membrane which is typical of prior art membranes as disclosed in European Patent No. 0 096 339 A2 to Bruschke.

The results may be tabulated as follows:

TABLE

| | | ISOPROPANOL | | |
| | | | Permeate | |
| Example | Membrane of Example | Feed Conc | Conc % IPA | Flux Kmh |
| --- | --- | --- | --- | --- |
| VII* | VII* | 75.7 | 1.73 | 0.573 |
| VIII* | VII* | 85.0 | 2.82 | 0.28 |
| IX* | VII* | 95.3 | 5.09 | 0.096 |
| X* | VII* | 98.6 | 9.72 | 0.024 |

From this tabulation of control examples using the prior art membrane system, it is apparent that as the feed concentration increases, the concentration of isopropanol in the permeated *undesirably* increases and the flux undesirably decreases. It is noted for example that using the charge concentration (85.0 w %) of applicants' preferred Example I applicants obtain a concentration of isopropanol in the permeate which is desirably smaller (i.e. only 34% as large) at a Flux which is desirably larger (i.e. by a factor of 3.6).

EXAMPLES XI*-XXVIII*

In this series of Examples, the charge is an aqueous ethanol solution at 70° C. and the membranes employed are the membranes of Examples I, III, and VIII*. The results may be tabulated as follows:

TABLE

| | | ETHANOL | | |
| | | Feed | Permeate | |
| Example | Membrane of Example | Conc % ETOH | Conc % ETOH | Flux Kmh |
| --- | --- | --- | --- | --- |
| XI* | VII* | 86.93 | 12.0 | 0.28 |
| XII* | VII* | 88.82 | 10.5 | 0.24 |
| XIII* | VII* | 89.60 | 10.1 | 0.23 |
| XIV* | VII* | 91.11 | 11.1 | 0.19 |
| XV* | VII* | 92.66 | 14.3 | 0.14 |
| XVI* | VII* | 93.01 | 16.5 | 0.15 |

TABLE

| Example | Membrane of Example | ETHANOL Feed Conc % ETOH | Permeate Conc % ETOH | Flux Kmh |
|---|---|---|---|---|
| XVII | I | 86.93 | 9.2 | 0.67 |
| XVIII | I | 88.82 | 14.1 | 0.40 |
| XIX | I | 89.60 | 11.0 | 0.49 |
| XX | I | 91.11 | 17.2 | 0.25 |
| XXI | I | 92.66 | 13.6 | 0.24 |
| XXII | I | 93.01 | 17.3 | 0.26 |

TABLE

| Example | Membrane of Example | ETHANOL Feed Conc % ETOH | Permeate Conc % ETOH | Flux Kmh |
|---|---|---|---|---|
| XXIII | III | 86.93 | 12.0 | 0.86 |
| XXIV | III | 88.82 | 17.8 | 0.51 |
| XXV | III | 89.60 | 24.8 | 0.29 |
| XXVI | III | 91.11 | 16.6 | 0.47 |
| XXVII | III | 92.66 | 18.9 | 0.37 |
| XXVIII | III | 93.01 | 22.9 | 0.39 |

From the above tables, it is apparent that it is possible to separate an aqueous solution of ethanol to yield a more concentrated solution of ethanol. For example, it is possible (Example XXIII) to treat a charge 86.93 w % aqueous solution of ethanol to yield a concentrated retentate plus a permeate containing only 12.0 w % ethanol at a Flux of 0.86. Treatment of the same charge (in control Example XI*) according to prior art techniques only gives a Flux of 0.28. Thus the instant invention permits attainment in this instance of results which are better than the prior art by a factor of 3+.

EXAMPLES XXIX*-LXXVI

In this series of examples, the procedure of Example I is utilized to prepare the membrane except that in place of the glutaraldehyde cross-linking agent there is used the same molar quantity of a different cross-linking agent as follows:

| Examples | Crosslinking Agent |
|---|---|
| XXIX*-XXXV* LVII*-LXI* | Maleic Acid* |
| XXXVI*-XLII* LXXII*-LXXVI* | Formaldehyde* |
| XLIII*-XLIX* LXVII*-LXXI* | Glyoxal* |
| L-LVI | 2-hydroxyhexanedial-1,6 |
| LXXII-LXXVI | Glutaraldehyde |

In Examples XXIX*-LVI, the charge aqueous solution is an aqueous solution of isopropanol at 70° C. The results may be tabulated as follows:

TABLE

| Example | ISOPROPANOL Feed Conc % iPrOH | Permeate Conc % iPrOH | Flux Kmh |
|---|---|---|---|
| XXIX* | 84.4 | 5.7 | 0.48 |
| XXX* | 86.83 | 1.9 | 0.33 |
| XXXI* | 89.45 | 2.0 | 0.19 |
| XXXII* | 91.66 | 2.1 | 0.09 |
| XXXIII* | 93.43 | 3.4 | 0.06 |
| XXXIV* | 92.24 | 6.3 | 0.04 |
| XXXV* | 98.77 | 29.2 | 0.005 |

TABLE

| Example | ISOPROPANOL Feed Conc % iPrOH | Permeate Conc % iPrOH | Flux Kmh |
|---|---|---|---|
| XXXVI* | 84.4 | 1.8 | 0.74 |
| XXXVII* | 86.83 | 1.5 | 0.49 |
| XXXVIII* | 89.45 | 0.94 | 0.29 |
| XXXIX* | 91.66 | 0.55 | 0.16 |
| XL* | 93.43 | 0.69 | 0.11 |
| XLI* | 92.24 | 0.83 | 0.06 |
| XLII* | 98.77 | 2.28 | 0.006 |

TABLE

| Example | ISOPROPANOL Feed Conc % iPrOH | Permeate Conc % iPrOH | Flux Kmh |
|---|---|---|---|
| XLIII* | 84.4 | 0.38 | 0.27 |
| XLIV* | 86.83 | 0.20 | 0.19 |
| XLV* | 89.45 | 0.06 | 0.12 |
| XLVI* | 91.66 | 0.03 | 0.05 |
| XLVII* | 93.43 | 0.06 | 0.04 |
| XLVIII* | 94.24 | 1.11 | 0.02 |
| XLIX* | 98.77 | 0.23 | 0.003 |

TABLE

| Example | ISOPROPANOL Feed Conc % iPrOH | Permeate Conc % iPrOH | Flux Kmh |
|---|---|---|---|
| L | 84.4 | 3.4 | 0.44 |
| LI | 86.83 | 2.7 | 0.35 |
| LII | 89.45 | 1.8 | 0.20 |
| LIII | 91.66 | 1.5 | 0.14 |
| LIV | 93.43 | 1.5 | 0.10 |
| LV | 94.24 | 1.2 | 0.06 |
| LVI | 98.77 | 3.3 | 0.007 |

From Examples XXIX*-LVI, it may be observed that in the separation of isopropyl alcohol, generally the concentration of isopropanol in the permeate is undesirably high and the Flux is undesirably low when using the control systems of Examples XXIX*-XLIX*. In contrast (Examples L-LVI), the concentration of isopropanol in the permeate is desirably low and the Flux is generally high when using the experimental system of this invention.

In Examples LVII*-LXXV, the charge aqueous solution is an aqueous solution of acetone at 50° C. The results may be tabulated as follows:

TABLE

| Example | ACETONE Feed Conc % AC | Permeate Conc % AC | Flux Kmh |
|---|---|---|---|
| LVII* | 80.71 | 3.2 | 0.96 |
| LVIII* | 83.85 | 2.2 | 0.91 |
| LIX* | 84.89 | 1.5 | 0.90 |
| LX* | 90.17 | 0.74 | 0.42 |

TABLE-continued

| | ACETONE | | |
|---|---|---|---|
| | Feed | Permeate | |
| Example | Conc % AC | Conc % AC | Flux Kmh |
| LXI* | 93.63 | 0.89 | 0.13 |

TABLE

| | ACETONE | | |
|---|---|---|---|
| | Feed | Permeate | |
| Example | Conc % AC | Conc % AC | Flux Kmh |
| LXII* | 80.71 | 6.7 | 0.92 |
| LXIII* | 83.85 | 3.7 | 0.80 |
| LXIV* | 84.89 | 2.7 | 0.72 |
| LXV* | 90.17 | 1.4 | 0.26 |
| LXVI* | 93.63 | 1.2 | 0.12 |

TABLE

| | ACETONE | | |
|---|---|---|---|
| | Feed | Permeate | |
| Example | Conc % AC | Conc % AC | Flux Kmh |
| LXVII* | 80.71 | 4.3 | 0.79 |
| LXVIII* | 83.85 | 2.0 | 0.82 |
| LXIX* | 84.89 | 1.2 | 0.77 |
| LXX* | 90.17 | 0.82 | 0.33 |
| LXXI* | 93.63 | 1.6 | 0.09 |

TABLE

| | ACETONE | | |
|---|---|---|---|
| | Feed | Permeate | |
| Example | Conc % AC | Conc % AC | Flux Kmh |
| LXXII | 80.71 | 12.3 | 0.95 |
| LXXIII | 83.85 | 7.6 | 0.83 |
| LXXIV | 84.89 | 6.6 | 0.81 |
| LXXV | 90.17 | 1.4 | 0.37 |
| LXXVI | 93.63 | 0.07 | 0.13 |

From the results of Examples LVII*-LXXVI, it is apparent that it is possible to effect separation of acetone-water solutions of various concentrations. It is for example possible to operate with a separation (Example LXXVI) which is significantly better than those of control Examples LVII*-LXXI*. It is possible to operate with a Flux which is high (Example LXXII).

EXAMPLE LXXVII

In this example, the selective separating layer is mounted on the porous support layer of a commercially available (from Film Tec Corp) composite containing a non-woven polyester backing as carrier layer bearing, as a porous support layer, a microporous polysulfone layer of molecular weight cut-off of 20,000. The selective separating layer is formed in situ by a one-step coating process. The separating layer is formed from a coating process. The separating layer is formed from a solution containing 10 g of 7 w % polyvinyl alcohol (m.w. of 115,000) in water to which is added 1.37 g of a 25 w % aqueous solution of glutaraldehyde and 0.15 g of 0.5N sulfuric acid solution. This mixture is stirred until homogeneous and spread onto the polysulfone microporous support to form a film 4 mils thick. The assembly is cured in an oven for 15 minutes at 150° C.

The membrane is evaluated in pervaporation cells to which the charge at 80° C. is an aqueous solution containing 85 w % ethylene glycol and 15 w % water. Permeate pressure is 5 mm.Hg. The permeate condenser contains 0.4 w % ethylene glycol at a flux of 0.68 kilograms per square meter per hour (kmh). A typical prior art membrane as disclosed in European patent No. 0 096 339 A2 has a permeate containing 4.7 w % ethylene glycol at a flux of 0.22 kmh.

TABLE

| | EG Content in permeate | Flux kmh |
|---|---|---|
| Example LXXVII | 0.4 | 0.68 |
| Prior Art - membrane of Example VII* | 4.7 | 0.22 |

From the above table, it is apparent that the instant invention makes it possible to attain permeate desirably containing as little as 0.4 w % of ethylene glycol—which is only (0.4/4.7) 8.5% of that attained by the prior art. It is also apparent that the flux attained in Example LXXVII is desirably more than three times that attained by the control prior art membrane of Example VII*.

Although this invention has been illustrated by reference to specific embodiments, it will be apparent to those skilled in the art that various charges and modifications may be made which clearly fall within the scope of the invention.

We claim:

1. The method of concentrating an aqueous charge including an organic oxygenate which comprises
    maintaining a non-porous separating layer of cast polyvinyl alcohol which has been cross-linked with an aliphatic polyaldehyde containing at least three carbon atoms including those in said aldehyde groups;
    maintaining a pressure drop across said non-porous separating layer of polyvinyl alcohol;
    passing an aqueous charge including an organic non-porous separating layer of polyvinyl alcohol whereby at least a portion of said water in said charge and a lesser portion of organic oxygenate in said charge pass by pervaporation through said non-porous separating layer of polyvinyl alcohol as a lean mixture containing more water and less organic oxygenate than are present in said charge and said charge is converted to rich liquid containing less water and more organic oxygenate than are present in said charge;
    recovering from the low pressure side of said non-porous separating layer of polyvinyl alcohol, said lean mixture containing more water and less organic oxygenate than are present in said charge, said lean mixture being recovered in vapor phase at a pressure below the vapor pressure thereof; and
    recovering from the high pressure side of said non-porous separating layer said rich liquid containing a lower water content and a higher organic oxygenate content than are present in said charge.

2. The method claimed in claim 1 wherein said aliphatic polyaldehyde is a $C_3$-$C_8$ aliphatic dialdehyde.

3. The method claimed in claim 1 wherein said aliphatic polyaldehyde is glutaraldehyde.

4. The method claimed in claim 1 wherein said organic oxygenate is a alcohol, acid, ester, ether, or ketone.

5. The method claimed in claim 1 wherein said organic oxygenate is an alcohol.

6. The method claimed in claim 1 wherein said organic oxygenate is isopropanol.

7. The method claimed in claim 1 wherein said organic oxygenate is ethanol.

8. The method claimed in claim 1 wherein said organic oxygenate is acetone.

9. The method claimed in claim 1 wherein said organic oxygenate is at least partially miscible with water.

10. The method claimed in claim 1 wherein said organic oxygenate is infinitely miscible with water.

11. The method claimed in claim 1 wherein said charge is a single phase charge.

12. The method claimed in claim 1 wherein said charge is a two phase charge.

13. The method claimed in claim 1 wherein said polyvinyl alcohol has a thickness of about 1-10 microns.

14. The method claimed in claim 1 wherein said polyvinyl alcohol which has been crosslinked is supported on a porous support layer.

15. The method in claim 14 wherein said porous support layer is a polysulfone polymer.

16. The method claimed in claim 14 wherein said porous support layer is a polysulfone polymer of molecular weight $M_n$ of 5,000-100,000 and of molecular weight cut off of less than about 25,000.

17. The method claimed in claim 14 wherein said porous support layer is a polysulfone polymer which is free of isopropylidene moieties in the backbone chain and wherein the backbone chain includes phenylene groups bonded only to sulfur and to oxygen.

18. The method of concentrating a charge aqueous solution of isopropyl alcohol which comprises maintaining a non-porous separating layer of cast polyvinyl alcohol which has been crosslinked with glutaraldehyde in the presence of sulfuric acid catalyst, said separating layer being supported on a porous supporting layer of polysulfone which is free of isopropylidene moieties;

maintaining a pressure drop across said separating layer and said porous support layer;

passing charge aqueous solution of isopropanol into contact with the high pressure side of said non-porous separating layer whereby at least a portion of the water in said charge aqueous solution and a lesser portion of isopropanol in said charge aqueous solution passes by pervaporation through non-porous separating layer of polyvinyl alcohol as a lean mixture containing more water and less ethylene glycol than are present in said charge aqueous solution and said charge aqueous solution is converted to a rich liquid containing less water and more isopropanol than are present in said charge aqueous solution;

recovering from the low pressure side of said non-porous separating layer said lean mixture containing more water and less isopropanol than are present in said charge aqueous solution, said lean mixture being recovered in vapor phase at a pressure below the vapor pressure thereof; and recovering from the high pressure side of said non-porous separating layer said rich liquid containing a lower water content and a higher isopropanol content than are present in said charge aqueous solution.

* * * * *

UNITED STATES PATENT AND TRADEMARK OFFICE
CERTIFICATE OF CORRECTION

PATENT NO. : 4,961,855

DATED : October 9, 1990

INVENTOR(S) : John Reale, Jr., Craig R. Bartels

It is certified that error appears in the above-identified patent and that said Letters Patent is hereby corrected as shown below:

Col. 2, line 14, correct the spelling of "isophoronediisocyanate"

Col. 14, line 40, after "organic", insert -- oxygenate into contact with the high pressure side of said --

Signed and Sealed this

Seventh Day of April, 1992

Attest:

HARRY F. MANBECK, JR.

*Attesting Officer*      *Commissioner of Patents and Trademarks*